US007618669B2

(12) United States Patent
Rangavajla et al.

(10) Patent No.: US 7,618,669 B2
(45) Date of Patent: Nov. 17, 2009

(54) LOW-LACTOSE PARTIALLY HYDROLYZED INFANT FORMULA

(75) Inventors: Nagendra Rangavajla, Newburgh, IN (US); Win-Chin Chiang, Newburgh, IN (US); Khaled A. Khatib, Newburgh, IN (US); David A. Wynsen, Newburgh, IN (US); Gabor Puski, Newburgh, IN (US); Jon Vanderhoof, Omaha, NE (US); Robert A. Burns, Evansville, IN (US)

(73) Assignee: Mead Johnson Nutrition Company, Evansville, IN (US)

( * ) Notice: Subject to any disclaimer, the term of this patent is extended or adjusted under 35 U.S.C. 154(b) by 772 days.

(21) Appl. No.: 11/142,544

(22) Filed: Jun. 1, 2005

(65) Prior Publication Data

US 2006/0286252 A1 Dec. 21, 2006

(51) Int. Cl.
*A23C 21/02* (2006.01)
*A23C 21/06* (2006.01)

(52) U.S. Cl. .......................... 426/583; 426/43; 426/580; 426/590; 426/801

(58) Field of Classification Search ................. 426/580, 426/583, 590, 601, 43, 801
See application file for complete search history.

(56) References Cited

U.S. PATENT DOCUMENTS

| 4,918,008 A | 4/1990 | Gauri ........................ 435/68.1 |
| 4,981,704 A | 1/1991 | Thibault ....................... 426/41 |
| 5,039,532 A | 8/1991 | Jost et al. ..................... 426/41 |
| 5,064,674 A | 11/1991 | Girsh ......................... 426/580 |
| 5,066,500 A | 11/1991 | Gil et al. ..................... 426/72 |
| 5,169,666 A | 12/1992 | Woychik ..................... 426/580 |
| 5,204,134 A | 4/1993 | Girsh ......................... 426/580 |
| 5,221,668 A | 6/1993 | Henningfield et al. ......... 514/23 |
| 5,382,439 A | 1/1995 | Hill et al. ..................... 426/73 |
| 5,405,637 A * | 4/1995 | Martinez et al. ............ 426/580 |
| 5,436,020 A | 7/1995 | Kuwata et al. .............. 426/583 |
| 5,438,042 A | 8/1995 | Schmidl et al. .............. 514/21 |
| 5,456,926 A | 10/1995 | Hill et al. ..................... 426/73 |
| 5,486,461 A | 1/1996 | Nielsen ..................... 435/68.1 |
| 5,492,899 A | 2/1996 | Masor et al. ................. 514/47 |
| 5,504,072 A | 4/1996 | Schmidl et al. .............. 514/21 |
| 5,587,399 A | 12/1996 | Acosta et al. ............... 514/561 |
| 5,589,357 A | 12/1996 | Martinez et al. ........... 435/68.1 |
| 5,602,109 A | 2/1997 | Masor et al. ................. 514/45 |
| 5,661,123 A | 8/1997 | Stalker et al. ................. 514/2 |
| 5,700,590 A | 12/1997 | Masor et al. ................ 426/656 |
| 5,709,888 A | 1/1998 | Gil et al. ..................... 424/522 |
| 5,744,179 A | 4/1998 | Shimamura et al. ........... 426/41 |
| 5,780,439 A | 7/1998 | Mendy et al. ................. 514/21 |
| 5,902,617 A | 5/1999 | Pabst ......................... 426/61 |
| 5,916,621 A | 6/1999 | Georgi et al. ............... 426/583 |
| 5,993,885 A | 11/1999 | Lin et al. .................... 426/583 |
| 6,017,550 A | 1/2000 | Berk et al. .................. 424/401 |
| 6,156,368 A | 12/2000 | Hayasawa et al. ........... 426/580 |
| 6,162,472 A * | 12/2000 | Griffin et al. .................. 426/42 |
| 6,171,621 B1 | 1/2001 | Braun et al. .................... 426/8 |
| 6,190,724 B1 | 2/2001 | Sawatzki et al. ............. 426/656 |
| 6,194,009 B1 | 2/2001 | Kamarel ...................... 426/72 |
| 6,365,218 B1 | 4/2002 | Borschel et al. ............. 426/573 |
| 6,395,508 B1 | 5/2002 | Shimamura et al. ........ 435/68.1 |
| 6,436,464 B1 | 8/2002 | Euber ......................... 426/654 |
| 6,465,209 B1 | 10/2002 | Blinkovsky et al. ........ 435/68.1 |
| 6,506,422 B1 | 1/2003 | Masson et al. ................. 426/2 |
| 6,511,696 B2 | 1/2003 | Gohman et al. ............. 426/601 |
| 6,605,310 B2 | 8/2003 | Fuchs et al. ................. 426/656 |
| 6,620,778 B2 | 9/2003 | Mallee et al. ................. 514/2 |
| 6,656,903 B1 | 12/2003 | Sawatzki et al. ............... 514/2 |
| 6,733,770 B1 | 5/2004 | Garcia-Rodenas et al. .. 424/439 |
| 6,737,076 B2 | 5/2004 | Fritsche et al. ............. 424/439 |
| 6,777,391 B1 | 8/2004 | Kratky et al. ................ 514/23 |
| 6,863,918 B2 | 3/2005 | Bindels et al. ............. 426/590 |
| 7,090,879 B2 * | 8/2006 | Albrecht et al. ............... 426/72 |
| 2003/0072863 A1 | 4/2003 | Hayasawa et al. |
| 2003/0138476 A1 | 7/2003 | Van Leeuwen et al. |
| 2003/0165606 A1 | 9/2003 | Lasekan et al. |
| 2004/0142017 A1 | 7/2004 | Luebbers |
| 2004/0213853 A1 | 10/2004 | Byard et al. |
| 2006/0286252 A1 * | 12/2006 | Rangavajla et al. ......... 426/580 |

FOREIGN PATENT DOCUMENTS

| EP | 0390 633 B1 | 12/1992 |
| EP | 0799577 A1 | 10/1997 |
| WO | WO 93/04593 | 3/1993 |
| WO | WO01/41581 A1 | 6/2001 |
| WO | 2004/112508 A1 * | 12/2004 |
| WO | WO2004/112508 A1 | 12/2004 |

OTHER PUBLICATIONS

Article from The Journal of Pediatrics, Nov. 1992, vol. 121, No. 5, part 2, pp. 90-94 by J. Roberto Moran entitled Effects of prolonged exposure to partially hydrolyzed milk protein.

(Continued)

*Primary Examiner*—Helen F Pratt
(74) *Attorney, Agent, or Firm*—Waddey & Patterson, P.C.; James R. Cartiglia

(57) ABSTRACT

The present invention relates to a low-lactose, partially hydrolyzed infant formula. The carbohydrate component of the infant formula comprises between 0% and 60% lactose and the protein component of the infant formula comprises partially hydrolyzed whey protein and casein, the protein component having a particular molecular weight.

21 Claims, No Drawings

OTHER PUBLICATIONS

Article from American Academy Pediatrics, Aug. 2000, vol. 106, No. 2, pp. 346-349 by Committee on Nutrition entitled Hypoallergenic Infant Formulas.

Article from American Journal Clinical Nutrition, 2003, vol. 78, pp. 296-301 by Olle Hernell et al. entitled Nutritional evaluation of protein hydrolysate formulas in healthy term infants: plasma amino acids, hematology, and trace elements[1-3].

Article from Arch Dis Child, 1999, vol. 81 pp. 80-84 by A. Host et al. entitled Dietary products used in infants for treatment and prevention of food allergy.

Article from Nestle Nutrition Workshop Series Pediatric Program, vol. 53, pp. 285-300, Nestec Ltd.; Veveys/S. Karger AG, Basel, 2004 by Andrea von Berg entitled The German Infant Nutritional Intervention Study[1] (GINI): A Model for Allergy Prevention.

Article from Journal Allergy Clinical Immunology, Mar. 2003, vol. 111(3) pp. 533-540 by A. von Berg et al. entitled The effect of hydrolyzed cow's milk formula for allergy prevention in the first year of life: the German Infant Nutritional Intervention Study, a randomized double-blind trial.

Article from Allergy, Aug. 1999, vol. 54, Issue 8, p. 837 by T. Vanto et al. entitled The patch test, skin prick test, and serum milk-specific IgE as diagnostic tools in cow's milk allergy in infants.

Article from Pediatric Allergy Immunology, Aug. 2000, vol. 11(3) pp. 149-161 by S. Halken et al. entitled Comparison of a partially hydrolyzed infant formula with two extensively hydrolyzed formulas for allergy prevention : a prospective, randomized study.

Article online by Gaining and Growing: Assuring Nutritional Care of Preterm Infants, entitled Infant Formulas. Online at http://depts.washington.edu/growing/Nourish/Formula.htm.

Article from Journal of the American Dietetic Association, Dec. 1999 by P. Z. Marincic et al. entitled Cow's-milk-based infant formula: Heterogeneity of bovine serum albumin content.

Article from Milchwissenschaft, Milk Science Int'l, Ava Agrar-Verlag Allgau,GMBH., Kempten, DE, vol. 59, No. 9/10, 2004, pp. 476-479, XP009068151 by C. Giardina ,et al. entitled Functional Properties of Milk Protein Hydrolysates Obtained by Controlled Enzymatic Hydrolysis.

* cited by examiner

LOW-LACTOSE PARTIALLY HYDROLYZED INFANT FORMULA

FIELD OF THE INVENTION

The present invention relates to low-lactose partially hydrolyzed infant formulas.

BACKGROUND

Food allergy is an immunologically mediated clinical syndrome that develops after the ingestion of a dietary product. The adverse reaction that accompanies a food allergy is often an immediate immunoglobulin E (IgE) mediated reaction, otherwise known as food protein allergy. Host, A., et al., *Dietary Products Used in Infants for Treatment and Prevention of Food Allergy*, Arch. Dis. Child 81:80-84 (1999). Symptoms of food protein allergy include angioedema, urticaria, eczema, asthma, rhinitis, conjunctivitis, vomiting, or anaphylaxis.

Cow's milk allergy is the most common food protein allergy in young children and occurs in about 2% to 3% of all infants. Sampson, H. A., *Food Allergy. Part* 1: *Immunopathogenesis and Clinical Disorders*, J Allergy Clin Immunol. 103:717-728 (1999). One possible explanation for the prevalence of cow's milk allergy among infants is that intact cow's milk protein, which is found in most conventional infant formulas, is the earliest and most common food allergen that infants are exposed to. In addition, infants may be especially susceptible to cow's milk allergy because their intestinal mucosa have a greater permeability to incompletely digested macromolecules than do adults. Moran R., *Effects of Prolonged Exposure to Partially Hydrolyzed Milk Protein*, J. Pediatr. 121:S90-S4 (1992).

While there is no known treatment that can completely cure cow's milk allergy, it may be possible to prevent or lessen cow's milk and other allergies in infants through the consumption of hydrolyzed protein formulas. It has been shown that the consumption of infant formulas having partially and extensively hydrolyzed proteins in place of conventional formulas having only intact proteins may reduce the risk of future allergies in infants. Id. Thus, if an infant has a family history of allergies, consumption of hydrolyzed protein formulas may reduce the risk of that child developing an allergy in the future.

Hydrolyzed protein formulas can be characterized as extensively hydrolyzed or partially hydrolyzed. Extensively hydrolyzed protein-containing infant formulas (EHF) are based on cow's milk, but the proteins have been treated with enzymes to break down most of the proteins that cause allergy-related symptoms. One example of a commercially-available EHF is Enfamil® Nutramigen®. It is a casein-based hypoallergenic infant formula for term infants who are sensitive to intact proteins in cow's milk and soy formulas. Partially hydrolyzed protein-containing infant formulas (PHF), on the other hand, have been treated with enzymes to break down only some of the milk proteins.

Ideally, any infant formula, including PHF, should simulate human milk as closely as possible. In human milk, there are two main proteins, whey protein and casein. Whey protein typically composes about 60% of the protein in human milk, while casein typically composese about 40%. Lonnerdal, B., *Biochemistry and Physiological Functions of Human Milk Proteins*, Am. J. Clin. Nutr. 42:1299-1317 (1985).

In addition to simulating the protein content of human milk, a PHF should not cause or exacerbate difficulties in carbohydrate absorption. The major carbohydrate in cow's milk-based infant formula is lactose. Lactose is a disaccharide of glucose and galactose and the enzyme lactase is required for the body to digest lactose. If lactase, which is located on the surface membrane of intestinal epithelial cells, is not present in sufficient amounts, the body may be unable to completely digest lactose. This condition, which is commonly known as lactose intolerance, can lead to symptoms such as abdominal bloating, gas, cramps and diarrhea.

One way to avoid the unwanted side effects of lactose intolerance in infants is to provide a low-lactose infant formula for nutritional supplementation or human milk replacement. A low-lactose infant formula typically has a small percentage of carbohydrates comprising lactose. The remaining carbohydrate content is derived from another source, such as corn syrup solids.

Various infant formulas have been disclosed, but none provide the combined benefits of the present invention. For example, U.S. Pat. No. 5,405,637 to Martinez, et al. relates to a milk protein partial hydrolysate and infant formula containing the same. The patent does not, however, disclose an infant formula having a lactose content between about 0% and 60%. Additionally, although the reference discloses a degree of hydrolysis between about 6 and 9%, the protein hydrolysate of the Martinez reference does not disclose having the molecular weight of the protein hydrolysate employed in the present invention.

U.S. Pat. No. 6,777,931 to Kratky relates to an infant formula composition having a low threonine content. While the reference discusses the use of whey protein and casein, the whey protein used is modified so that the caseino-glyo-macropeptide (cGMP) has been removed. Additionally, the reference does not disclose an infant formula having a partial hydrolysate with the particular molecular weight profile as in the present invention.

U.S. Pat. No. 6,162,472 to Griffin, et al. relates to an infant formula comprised of casein and whey protein and having a lactose content of less than 20%, but does not disclose a partial hydrolysate formula.

U.S. Pat. No. 6,171,621 to Braun, et al., U.S. Pat. No. 6,863,918 to Bindels, et al., and U.S. Pat. No. 6,194,009 to Kamarel all relate to various infant formulas and nutritional products based on protein hydrolysates. The patents do not, however, disclose a supplement or formula having a whey protein:casein ratio between about 50:50 and 70:30. Additionally, the partial hydrolysates of the various patents do not disclose hydrolysates with the molecular weight employed in the present application.

SUMMARY OF THE INVENTION

Briefly, the present invention is directed to a novel infant formula comprising a carbohydrate component comprised of between about 0% and 60% lactose, wherein said percentages are based on the total weight of the carbohydrates present in the formula; and a protein component of partially hydrolyzed whey protein and casein, wherein the ratio of whey protein to casein is between about 50:50 and 70:30 and wherein the protein hydrolysate has the peptides spread over the range of molecular weight distribution, as a function of their molar mass, that is shown in Table 1.

TABLE 1

| Molar Mass (in Daltons) | % Molecular Weight Distribution |
|---|---|
| <500 | 11-20 |
| 500-1000 | 25-38 |

TABLE 1-continued

| Molar Mass (in Daltons) | % Molecular Weight Distribution |
|---|---|
| 1000-2000 | 27-30 |
| 2000-3000 | 8-16 |
| 3000-5000 | 3-10 |
| >5000 | 2-11 |

Among the several advantages found to be achieved by the present invention, the milk protein partial hydrolysate has a protein composition similar to that of human milk, an improved taste, and improved emulsifying properties. Additionally, the present invention induces a lesser priming effect for IgG antibody response than does intact cow's milk. Thus, the present invention may have a reduced immunogenic potential.

DETAILED DESCRIPTION OF THE PREFERRED EMBODIMENTS

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used on another embodiment to yield a still further embodiment.

Thus, it is intended that the present invention cover such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Definitions

As used herein, the term "low-lactose" means a lactose content that is less than 100%, including 0% lactose.

The terms "degree of hydrolysis" mean the extent to which peptide bonds are broken by an enzymatic hydrolysis reaction. The measurement shows the number of specific peptide bonds broken in hydrolysis as a percent of the total number of specific peptide bonds present in the intact protein.

The term "probiotic" means a microorganism that exerts beneficial effects on the health of the host.

As used herein, the term "prebiotic" means a non-digestible food ingredient that beneficially affects the host by selectively stimulating the growth and/or activity of one or a limited number of bacteria in the colon that can improve the health of the host.

The term "subject" means any mammal, preferably a human.

As used herein, the term "infant" means a human that is less than about one year old.

As used herein, the term "infant formula" means a composition that satisfies the nutrient requirements of an infant by being a substitute for human milk. In the United States, the content of an infant formula is dictated by the federal regulations set forth at 21 C.F.R. Sections 100, 106, and 107. These regulations define macronutrient, vitamin, mineral, and other ingredient levels in an effort to stimulate the nutritional and other properties of human breast milk.

Invention

In accordance with the present invention, a novel infant formula has been discovered. The infant formula has a low lactose content and comprises a mixture of partially hydrolyzed casein and whey protein. The protein partial hydrolysate of the infant formula has a specific and unique molecular weight distribution that results in a product that is distinct from the prior art.

The present invention provides a whey protein:casein ratio that is similar to that found in human breast milk. In a particular embodiment, the ratio of whey protein:casein is between about 50:50 and 70:30. In another embodiment, the ratio of casein:whey protein is about 60:40.

The whey protein used in the present invention may be derived from any source known in the art. In one embodiment, the whey protein may be sourced from a raw whey obtained from sweet cheese manufacturing, from whey protein concentrate (WPC) which is obtained by ultrafiltration (UF whey), by ion exchange and/or electrophoresis (ED whey) or from whey isolate that has been treated to reduce the lactose content of the whey.

The casein used in the present invention may also be derived from any source known in the art. For example, the casein can be either acid casein or non-fat milk solids (NFM).

Both the whey protein and the casein may be diluted or reconstituted to solutions containing between about 20% and 25% total solids, and between about 40% and 50% protein on a dry basis.

In the present invention, the carbohydrate component comprises between about 0% and 60% lactose. In another embodiment of the present invention, the carbohydrate component comprises between about 15% and 55% lactose. In yet another embodiment of the present invention, the carbohydrate component comprises between about 20% and 30% lactose. In a particular embodiment of the invention, the carbohydrate component comprises between about 1 and 25% lactose. In these embodiments, the remaining source of carbohydrates may be any carbohydrate source known in the art, such as lactose, glucose, corn syrup solids, maltodextrins, sucrose, starch, rice syrup solids, and the like. In a particular embodiment, the carbohydrate component comprises about 25% lactose and about 75% corn syrup solids.

The lactose may be added to the infant formula or may be present naturally in the components of the infant formula. In one embodiment of the invention, the lactose in naturally present in the dried hydrolysate. In this embodiment, between about 30% and 70% of the dried hydrolysate may constitute carbohydrates. In a particular embodiment, about 50% of the dried hydrolysate constitutes carbohydrate.

In one embodiment of the invention, the lactose content can be 0%. In this embodiment, the hydrolysate can be treated using any method known in the art to remove its lactose content. Alternatively, milk protein ingredients that are lactose-free can be used to prepare the infant formula.

In the present invention, the proteins are hydrolyzed using a proteolytic enzyme, Protease N. Protease N "Amano" is commercially available from Amano Enzyme U.S.A. Co., Ltd., Elgin, Ill. Protease N is a proteolytic enzyme preparation that is derived from the bacterial species *Bacillus subtilis*. The protease powder is specified as "not less than 150,000 units/g", meaning that one unit of Protease N is the amount of enzyme which produces an amino acid equivalent to 100 micrograms of tyrosine for 60 minutes at a pH of 7.0. To produce the infant formula of the present invention, Protease N can be used at levels of about 0.5% to about 1.0% by weight of the total protein being hydrolyzed.

The protein hydrolysis by Protease N is typically conducted at a temperature of about 50° C. to about 60° C. The hydrolysis occurs for a period of time so as to obtain a degree of hydrolysis between about 4% and 10%. In a particular embodiment, hydrolysis occurs for a period of time so as to obtain a degree of hydrolysis between about 6% and 9%. In another embodiment, hydrolysis occurs for a period of time so as to obtain a degree of hydrolysis of about 7.5%. This level of hydrolysis may take between about one half hour to about 3 hours.

A constant pH should be maintained during hydrolysis. In the method of the present invention, the pH is adjusted to and maintained between about 6.5 and 8. In a particular embodiment, the pH is maintained at about 7.0.

In order to maintain the optimal pH of the solution of whey protein, casein, water and Protease N, a caustic solution of sodium hydroxide and/or potassium hydroxide can be used to adjust the pH during hydrolysis. If sodium hydroxide is used to adjust the pH, the amount of sodium hydroxide added to the solution should be controlled to the level that it comprises less than about 0.3% of the total solid in the finished protein hydrolysate. A 10% potassium hydroxide solution can also be used to adjust the pH of the solution to the desired value, either before the enzyme is added or during the hydrolysis process in order to maintain the optimal pH.

The amount of caustic solution added to the solution during the protein hydrolysis can be controlled by a pH-stat or by adding the caustic solution continuously and proportionally. The hydrolysate can be manufactured by standard batch processes or by continuous processes.

To better ensure the consistent quality of the protein partial hydrolysate, the hydrolysate is subjected to enzyme deactivation to end the hydrolysis process. The enzyme deactivation step may consist include at heat treatment at a temperature of about 82° C. for about 10 minutes. Alternatively, the enzyme can be deactivated by heating the solution to a temperature of about 92° C. for about 5 seconds. After enzyme deactivation is complete, the hydrolysate can be stored in a liquid state at a temperature lower than 10° C.

In an embodiment of the present invention, the liquid partial protein hydrolysate made according to the methods described herein can be used as is and blended with other ingredients to make an infant formula. Alternatively, the partial hydrolysate can be produced in powder form by spray drying the liquid hydrolysate. The spray-dried hydrolysate can then be incorporated into an infant formula. In another embodiment, the liquid partial hydrolysate can be concentrated by evaporation and then spray dried. Again, the spray-dried hydrolysate can be incorporated into an infant formula. An infant formula having the described partially hydrolyzed proteins can be formulated using any of the methods of infant formula formulation known in the art.

The infant formula of the present invention may be nutritionally complete and typically contains suitable types and amounts of lipid, carbohydrate, protein, vitamins and minerals. The amount of lipid or fat typically can vary from about 3 to about 7 g/100 kcal. Lipid sources can be any known in the art, including vegetable oils such as palm oil, soybean oil, palmolein, coconut oil, medium chain triglyceride oil, high oleic sunflower oil, high oleic safflower oil, and the like. The amount of protein typically can vary from about 1 to about 5 g/100 kcal. The amount of carbohydrate typically can vary from about 8 to about 12 g/100 kcal.

The infant formula may include a probiotic. Any probiotic known in the art will be acceptable in this embodiment. In a particular embodiment, the probiotic is chosen from the group consisting of *Lactobacillus* and *Bifidobacterium*.

In another embodiment of the invention, the infant formula may contain one or more prebiotics. Any prebiotic known in the art will be acceptable in this embodiment. Prebiotics of the present invention may include lactulose, galacto-oligosaccharide, fructo-oligosaccharide, isomalto-oligosaccharide, soybean oligosaccharides, lactosucrose, xylo-oligosacchairde, and gentio-oligosaccharides.

In other embodiments of the present invention, the infant formula may contain other components such as long chain polyunsaturated fatty acids (LCPUFA). Suitable LCPUFAs include, but are not limited to, α-linoleic acid, γ-linoleic acid, linoleic acid, linolenic acid, eicosapentaenoic acid (EPA), arachidonic acid (ARA) and docosahexaenoic acid (DHA). In an embodiment, the infant formula contains DHA. In another embodiment, the infant formula contains ARA. In yet another embodiment, the infant formula of the invention contains both DHA and ARA.

In one embodiment, both DHA and ARA are incorporated into the infant formula of the present invention. In this embodiment, the weight ratio of ARA:DHA is typically from about 1:3 to about 9:1. Alternatively, this ratio can be from about 1:2 to about 4:1. In yet another alternative, the ratio can be from about 2:3 to about 2:1. In one particular embodiment, the ratio is about 2:1.

The effective amount of DHA in an embodiment of the present invention is typically from about 3 mg per kg of body weight per day to about 150 mg per kg of body weight per day. In one embodiment of the invention, the amount of DHA is from about 6 mg per kg of body weight per day to about 100 mg per kg of body weight per day. In another embodiment, the amount is from about 10 mg per kg of body weight per day to about 60 mg per kg of body weight per day. In yet another embodiment, the amount is from about 15 mg per kg of body weight per day to about 30 mg per kg of body weight per day.

The amount of DHA in infant formulas for use with the present invention typically varies from about 5 mg/100 kcal to about 80 mg/100 kcal. In one embodiment of the present invention the amount of DHA varies from about 10 mg/100 kcal to about 50 mg/100 kcal; and in another embodiment it varies from about 15 mg/100 kcal to about 20 mg/100 kcal. In a particular embodiment of the present invention, the amount of DHA is about 17 mg/100 kcal.

The effective amount of ARA in an embodiment of the present invention is typically from about 5 mg per kg of body weight per day to about 150 mg per kg of body weight per day. In one embodiment of this invention, the amount of ARA varies from about 10 mg per kg of body weight per day to about 120 mg per kg of body weight per day. In another embodiment, the amount varies from about 15 mg per kg of body weight per day to about 90 mg per kg of body weight per day. In yet another embodiment, the amount varies from about 20 mg per kg of body weight per day to about 60 mg per kg of body weight per day.

The amount of ARA in infant formulas for use with the present invention typically varies from about 10 mg/100 kcal to about 100 mg/100 kcal. In one embodiment of the present invention, the amount of ARA varies from about 15 mg/100 kcal to about 70 mg/100 kcal. In another embodiment the amount of ARA varies from about 20 mg/100 kcal to about 40 mg/100 kcal. In a particular embodiment of the present invention, the amount of ARA is about 34 mg/100 kcal.

DHA and ARA can be supplemented into the present invention using standard techniques known in the art. For example, DHA and ARA can be added to the supplement or formula by replacing an equivalent amount of an oil, such as high oleic sunflower oil, normally present in the formula. As another example, the oils containing DHA and ARA can be added to the supplement or formula by replacing an equivalent amount of the rest of the overall fat blend normally present in the formula without DHA and ARA.

The source of DHA and ARA can be any source known in the art. In an embodiment of the present invention, sources of DHA and ARA are single cell oils as taught in U.S. Pat. Nos. 5,374,567; 5,550,156; and 5,397,591, the disclosures of which are incorporated herein in their entirety by reference. However, the present invention is not limited to only such oils. DHA and ARA can be in natural or refined form.

In one embodiment, the source of DHA and ARA is substantially free of eicosapentaenoic acid (EPA). For example, in one embodiment of the present invention the infant formula contains less than about 16 mg EPA/100 kcal; in another embodiment less than about 10 mg EPA/100 kcal; and in yet another embodiment less than about 5 mg EPA/100 kcal. One particular embodiment contains substantially no EPA. Another embodiment is free of EPA in that even trace amounts of EPA are absent from the formula.

The infant formula of the present invention has a particular molecular weight distribution. This molecular weight distribution has demonstrated acceptable emulsification and taste qualities as compared to other partial hydrolysates found in the prior art. In addition, the particular molecular weight distribution has been shown to induce a lesser serum IgG antibody effect than intact milk protein.

In an embodiment of the present invention, the partial protein hydrolysate made according to the methods described herein can be incorporated into a nutritional supplement. The partial protein hydrolysate can be used in liquid form and blended with other ingredients to make a liquid nutritional supplement. Alternatively, the partial protein hydrolysate can be spray-dried and incorporated into a powdered nutritional supplement. A nutritional supplement having the described partially hydrolyzed proteins can be formulated using any of the methods of nutritional supplement formulation known in the art.

Size exclusion chromatography (SEC) was used to determine the molecular weight distribution of the hydrolysate peptides created by the presently-described hydrolysis process. Specifically, a sufficient amount of the powdered infant formula was weighed out to provide 0.5 grams of protein into a 50 ml conical centrifuge tube. Water was added to bring the tube to a volume of 45 ml. The mixture was placed in a Sarstedt D-5223 Mixer and mixed for one hour. After mixing, a 1% protein solution was created by adding another 5 ml of water to the tube. A stock standard was prepared and mixed for one hour as well.

Separately, 14.91 grams potassium chloride (KCl) was added to a 1000 ml beaker. The KCl was dissolved by adding 700 ml of water to the beaker. 250 ml acetonitrile and 1.0 ml trifloroacetic acid were then added to the KCl solution (eluent). The pH was adjusted to 3.0 using a 0.2M $K_2HPO_4$ solution.

An HPCL reagent bottle was filled and the bottle was washed with eluent, reserving about 50 ml for dilution of samples and standards. The Hitachi L-6200 A Intelligent Pump lines were purged with eluent and the columns were equilibrated with eluent for one hour.

After the samples were mixed for one hour, 5.0 ml of each sample was pipetted into glass screw-cap tubes. 5.0 ml Dichloromethane was also pipetted into each tube. The tubes were capped and mixed by inversion four times. The samples were then centrifuged for five minutes at 200×g.

While the samples were in the centrifuge, the stock standards 1-5 were diluted with eluent (800 ul+3200 ul). Approximately 1 ml of each standard was pipetted into each of two autosampler vials and capped.

The upper (aqueous) layer of the centrifuged samples 1-10 were diluted with eluent (100 ul+900 ul). The vials were loaded into the autosampler tray as follows: blank, standard, samples and second standard. The tray was placed in the Hitachi autosampler. The total number of vials to be run were entered into the autosampler program using the keys on the front of the autosampler and the samples were run. The results indicated the molecular weight profile of the protein.

In an embodiment, the partial hydrolysate of the invention has an average molecular weight of 2,000 with the range of molecular weight distribution shown in Table 1, above.

In another embodiment, the partial hydrolysate of the invention has the molecular weight distribution shown in Table 2.

TABLE 2

| Molar Mass (in Daltons) | % Molecular Weight Distribution |
|---|---|
| <500 | 17 |
| 500-1000 | 35.1 |
| 1000-2000 | 30.9 |
| 2000-3000 | 9.6 |
| 3000-5000 | 4.2 |
| >5000 | 2.8 |

The following examples describe various embodiments of the present invention. Other embodiments within the scope of the claims herein will be apparent to one skilled in the art from consideration of the specification or practice of the invention as disclosed herein. It is intended that the specification, together with the examples, be considered to be exemplary only, with the scope and spirit of the invention being indicated by the claims which follow the examples. In the examples, all percentages are given on a weight basis unless otherwise indicated.

EXAMPLE 1

This example illustrates a method for producing a protein partial hydrolysate. Initially, 60.3 kg non-milk solids (milk powder) and 37.4 kg whey protein concentrate (60%) were intermixed in a tank containing water at 54° C. The slurry had a total solids content of between 20% and 23%. The pH of the slurry was then measured. Sodium and potassium hydroxide were added to the slurry to adjust the pH of the slurry to 7.0. After adjusting the pH, 0.5 kg of Amano N enzyme was added to the slurry. Following the addition of Amano N to the slurry, the pH was continuously adjusted to a pH of 7.0 using sodium hydroxide and potassium hydroxide. The total amount of sodium hydroxide added to the slurry was 0.3 kg. The total amount of potassium hydroxide added to the slurry was 1.5 kg.

The hydrolysis was permitted to occur for 90 minutes, the time starting with the addition of Amano N enzyme to the slurry. At the end of 90 minutes, the slurry was heat treated to inactivate the enzyme. The heat treatment consisted of raising the temperature of the slurry to 82° C. for 10 minutes. The degree of hydrolysis obtained in this example was between 6% and 9%. The slurry was then cooled and spray dried to obtain a powdered hydrolysate.

EXAMPLE 2

This example illustrates one embodiment of ingredients that can be used to prepare the infant formula of the present invention.

TABLE 3

Recipe of an Embodiment of the Hydrolysate

| Ingredient | Kg per 100 kg dried hydrolysate |
|---|---|
| Nonfat Milk Solids | 60.3 |
| Whey Protein Concentrate | 37.4 |
| Potassium Hydroxide | 1.5 |
| Enzyme (Amano N) | 0.5 |
| Sodium Hydroxide | 0.3 |

Vitamins may be added to the ingredients in Table 3. Examples of vitamins that can be added to the formula include vitamin A, vitamin $D_3$, vitamin E, vitamin $K_1$, thiamin, riboflavin, vitamin $B_6$ hydrochloride, vitamin $B_{12}$, niacinamide, folic acid, calcium pantothenate, biotin and ascorbic acid.

Minerals may also be added to the ingredients in Table 3. Examples of minerals that can be added to the formula include calcium phosphate, calcium glycerophosphate, calcium gluconate, sodium citrate, potassium chloride, potassium citrate, potassium phosphate, magnesium phosphate, ferrous sulfate, zinc sulfate and cupric sulfate.

EXAMPLE 3

This example illustrates the priming effect for IgG antibody response of the protein partial hydrolysate obtained in Example 1. Three hundred twenty-three infants were studied in seven pediatric practices located throughout the United States. Subjects were healthy term infants enrolled shortly after birth.

Infants whose mother indicated her intention to breastfeed were assigned to group A. Those infants whose mothers elected not to breastfeed were randomly assigned in double-blind fashion to either group B or C. Infants in group B received an infant formula comprising the protein partial hydrolysate obtained in Example 1. Infants in group C received a commercially available, whey-protein dominant milk-based formula (Enfamil, available from Mead Johnson Co., Evansville, Ind.). Both formulas contained the same amounts of protein, carbohydrate and fat.

Infants were evaluated at monthly intervals up to 4 months of age at all sites, and at 6 and 8 months of age at three of the seven sites. Blood was drawn on admission and at 3, 6 and 8 months of age for detection of serum antibodies to milk. IgE anti-milk protein antibodies were quantified by a biotin-avidin enzyme-linked immunosorbent assay; IgG anti-milk protein antibodies were determined by use of enzyme-linked immunosorbent assay described in Burks, et al. Burks, A. W., et al., *Antibody Response to Milk Protein in Patients with Milk Protein Intolerance Documented by Challenge*, J. Allergy Clin. Immunol. 85:921-927 (1990). Additional blood was drawn to measure serum levels of ferritin and hemoglobin and determine hematocrit in the infants who were examined at 8 months of age.

The mean serum concentration of IgG antibodies to milk was comparable in all groups at the time of admission to the study. However, increases in serum IgG antibodies to milk were significantly larger in the group of infants fed formula C than those fed breast milk (group A) or formula B. This lower concentration of IgG antibodies to milk in group B indicates a greater priming effect of intact cow milk protein for IgG antibody responses (group C). Thus, there may be a reduced immunogenic potential of the partially hydrolyzed milk proteins of group B.

At the time of enrollment, no significant differences among the three groups were found in the mean serum concentrations of IgE antibodies to milk. Further there were no significant differences in the IgE levels among the feeding regimens throughout the study. The mean serum ferritin, heatocrit and hemoglobin values were within the normal range at 8 months of age, and no significant differences were found among the three groups.

EXAMPLE 4

This example illustrates a particular embodiment of an infant formula supplemented with the protein partial hydrolysate prepared according to the process of the present invention. In this example, lactose comprises about 23.5% of the carbohydrate component.

TABLE 4

Nutrient Information for Infant formula

| Ingredient | Per 100 kg |
|---|---|
| Corn Syrup Solids | 44.256 kg |
| Partially Hydrolyzed NFM and WPC solids | 26.865 kg |
| Fat Blend | 26.628 kg |
| Single Cell ARA and DHA Oil Blend | 0.709 kg |
| Calcium Carbonate | 0.400 kg |
| Calcium Phosphate, tribasic | 0.200 kg |
| Potassium Chloride | 0.200 kg |
| Choline Chloride | 0.134 kg |
| Magnesium Phosphate | 0.100 kg |
| L-Carnitine | 0.010 kg |
| Ascorbic Acid | 162.900 g |
| Inositol | 39.887 g |
| Taurine | 33.875 g |
| Tocopheryl Acetate | 25.278 g |
| Vitamin A | 7.871 g |
| Niacimamide | 6.475 g |
| Vitamin $K_1$ | 5.454 g |
| Calcium Pantothenate | 3.299 g |
| Vitamin $B_{12}$ | 2.122 g |
| Biotin Trituration | 1.608 g |
| Vitamin D3 | 0.969 g |
| Riboflavin | 0.755 g |
| Thiamin HCl | 0.601 g |
| Pyridoxine HCl | 0.518 g |
| Folic Acid | 0.122 g |
| Ferrous Sulfate, Heptahydrate | 49.600 g |
| Lactose | 138.017 g |
| Zinc Sulfate | 16.422 g |
| Sodium Selenite | 0.018 g |
| Cupric Sulfate | 1.688 g |
| Manganese Sulfate | 0.239 g |

In this example, lactose is naturally present in the partially hydrolyzed NFM and WPC solids. More specifically, about 50% of the partially hydrolyzed NFM and WPC solids constitutes lactose. Thus, the amount of lactose present in those NFM and WPC solids is approximately 13.433 kg. There are an additional 138.017 g lactose present in the composition. This totals approximately 13.571 kg lactose in the infant formula.

There are 44.256 kg of corn syrup solids present in the infant formula. The total carbohydrate content is 57.827 kg, lactose comprising only 13.571 kg of that total. Therefore, lactose comprises approximately 23.5% of the total carbohydrate content in the infant formula.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged both in whole or in part. For example, while methods for the production of a sterile liquid infant formula made according to those methods have been exemplified, other uses are contemplated. Therefore, the spirit and scope of the appended claims should not be limited to the description of the preferred versions contained therein.

What is claimed is:

1. An infant formula comprising:
a carbohydrate component which is comprised of between about 0% and 60% lactose, based on the total weight of the carbohydrates present in the infant formula; and
a protein component which is comprised of partially hydrolyzed whey protein and casein, wherein the ratio of whey protein to casein is between about 50:50 and 70:30 and wherein the protein hydrolysate has the peptides spread over the following range of molecular weight distribution as a function of their molar mass:

| Molar Mass (in Daltons) | % Molecular Weight Distribution |
| --- | --- |
| <500 | 11-20 |
| 500-1000 | 25-38 |
| 1000-2000 | 27-30 |
| 2000-3000 | 8-16 |
| 3000-5000 | 3-10 |
| >5000 | 2-11. |

2. The infant formula according to claim 1, wherein the protein hydrolysate has the peptides spread over the following molecular weight distribution as a function of their molar mass:

| Molar Mass (in Daltons) | % Molecular Weight Distribution |
| --- | --- |
| <500 | 17 |
| 500-1000 | 35.1 |
| 1000-2000 | 30.9 |
| 2000-3000 | 9.6 |
| 3000-5000 | 4.2 |
| >5000 | 2.8. |

3. The infant formula according to claim 1, wherein the ratio of whey protein:casein is about 60:40.

4. The infant formula according to claim 1, wherein the carbohydrate component comprises between about 15% and 55% lactose.

5. The infant formula according to claim 1, wherein the carbohydrate component comprises between about 20% and 30% lactose.

6. The infant formula according to claim 1, wherein the carbohydrate component comprises about 25% weight percent lactose and about 75% weight percent corn syrup solids.

7. The infant formula according to claim 6, wherein the degree of hydrolysis of the protein component is between about 6% and 9%.

8. The infant formula according to claim 1, wherein the degree of hydrolysis of the protein component is between about 4% and 10%.

9. The infant formula according to claim 1, wherein the infant formula additionally comprises at least one probiotic.

10. The infant formula according to claim 1, wherein the infant formula additionally comprises at least one prebiotic.

11. The infant formula according to claim 10, wherein the LCPUFA comprises DHA and ARA.

12. The infant formula according to claim 1, wherein the infant formula additionally comprises a LCPUFA.

13. The infant formula according to claim 12, wherein the LCPUFA comprises DHA or ARA.

14. The infant formula according to claim 12, wherein the LCPUFA comprises DHA in an amount of between about 3 mg per kg of body weight per day to about 150 mg per kg of body weight per day.

15. The infant formula according to claim 12, wherein the LCPUFA comprises ARA in an amount of between about 5 mg per kg of body weight per day to about 150 mg per kg of body weight per day.

16. The infant formula according to claim 15, wherein the ratio of ARA:DHA is from about 1:3 to about 9:1.

17. The infant formula according to claim 15, wherein the ratio of ARA:DHA is from about 1:2 to about 4:1.

18. The infant formula according to claim 15, wherein the ratio of ARA:DHA is from about 2:3 to about 2:1

19. The infant formula according to claim 1, wherein the infant formula is in powdered form.

20. The infant formula according to claim 1, wherein the infant formula is in liquid form.

21. A method for preventing the onset of allergies in a subject, the method comprising administering to the subject an infant formula according to claim 1.

* * * * *

UNITED STATES PATENT AND TRADEMARK OFFICE
CERTIFICATE OF CORRECTION

PATENT NO.      : 7,618,669 B2                                           Page 1 of 1
APPLICATION NO. : 11/142544
DATED           : November 17, 2009
INVENTOR(S)     : Rangavajla et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1038 days.

Signed and Sealed this

Twenty-sixth Day of October, 2010

David J. Kappos
*Director of the United States Patent and Trademark Office*